United States Patent [19]

Feld

[11] 4,106,477
[45] Aug. 15, 1978

[54] THERAPEUTIC SELF-GENERATING MOIST HEAT PAD

[75] Inventor: Sheldon L. Feld, Jamaica, N.Y.

[73] Assignee: Chem-E-Watt Corporation, Racine, Wis.

[21] Appl. No.: 460,492

[22] Filed: Apr. 12, 1974

[51] Int. Cl.[2] .............................. F24J 1/04; F24J 3/04
[52] U.S. Cl. .................................... 126/263; 44/3 A; 126/204
[58] Field of Search ...................... 126/263, 204; 44/3; 219/224; 128/399, 403

[56] References Cited

U.S. PATENT DOCUMENTS

| | | | |
|---|---|---|---|
| 2,018,367 | 10/1935 | Lackenbach | 44/3 A |
| 2,710,008 | 6/1955 | Jensen | 126/204 |
| 2,725,060 | 11/1955 | Pazul | 44/3 R X |
| 2,935,983 | 5/1960 | Reik | 126/263 |
| 3,207,149 | 9/1965 | Spindler | 126/263 |
| 3,314,413 | 4/1967 | Cambridge | 126/263 |
| 3,774,589 | 11/1973 | Kober | 44/3 A X |

*Primary Examiner*—William F. O'Dea
*Assistant Examiner*—Harold Joyce
*Attorney, Agent, or Firm*—St. Onge, Steward, Johnston, Reens & Noë

[57] ABSTRACT

A water activated therapeutic moist heat pad structure is described formed with outer porous water retaining layers which enclose an inner layer of distributed heat generating heat cells and an associated water retaining absorbent inner porous layer. In a preferred embodiment the heat cells are formed of electrochemical heat cells wherein a suitable dry electrolyte is provided such as table salt. The inner porous layer is sized to provide the electrochemical heat cells with adequate electrolyte to use up their active ingredients and achieve an extended heating period. The segmentation of the heat cells and their distribution throughout the structure combine to provide a flexible therapeutic moist heating pad which can conform to the body surface to be treated.

26 Claims, 4 Drawing Figures

U.S. Patent Aug. 15, 1978 4,106,477
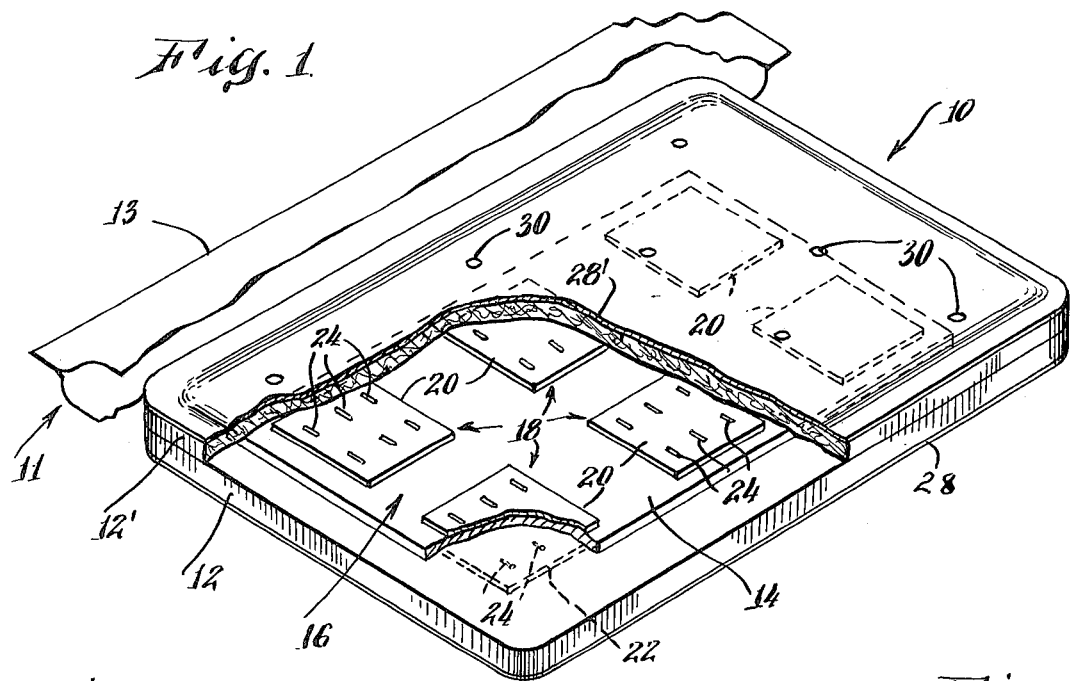
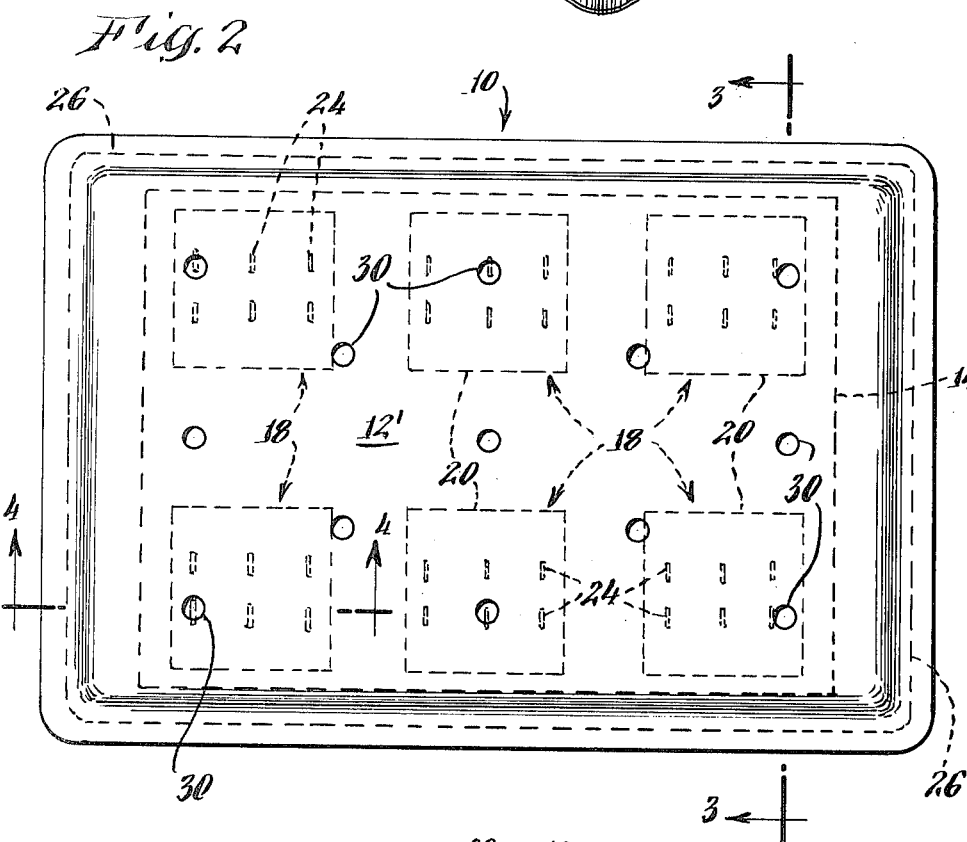
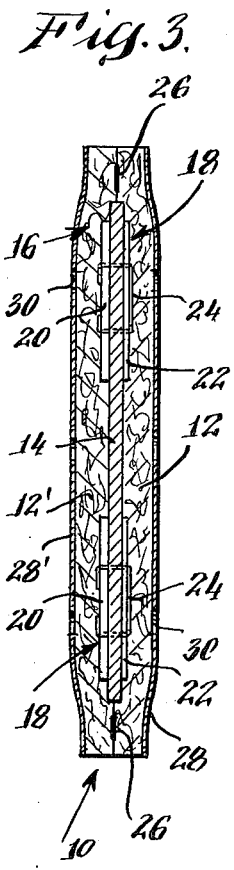
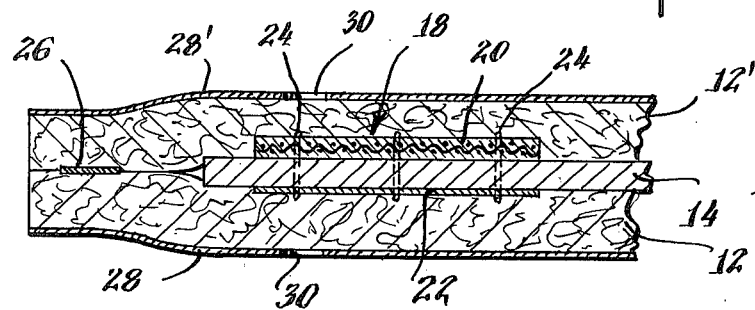

THERAPEUTIC SELF-GENERATING MOIST HEAT PAD

This invention relates to a therapeutic heating pad. More specifically, this invention relates to a therapeutic heating pad capable of generating moist heat.

BACKGROUND OF THE INVENTION

Many different heating pad types are known in the art. One kind of heating pad generates heat with a chemical mixture operating in an exothermic reaction. Many such heaters have been described starting with the heating pad of Allison as disclosed in his 1907 U.S. Pat. No. 858,848. Other exothermic heating pads are described in such patents as to Mendez U.S. Pat. No. 2,612,155; Smith U.S. Pat. No. 1,620,581; Meagher U.S. Pat. No. 1,899,286; Baysinger U.S. Pat. No. 1,819,807; Glasser U.S. Pat. No. 3,301,250, and many others.

One version of exothermic heating pads involves a multiple compartment for the respective storage of chemicals and water. Activation of such device is obtained by squeezing to rupture a compartment (Foster U.S. Pat. No. 2,157,169) and cause an intermingling of the chemicals and water. Another multiple compartment exothermic heater or refrigerating device is described in Spencer U.S. Pat. No. 3,542,032.

The multiple compartment heating pad structure tends to be complex and creates the probability of premature rupture of the frangible partition, thus resulting in a premature activation of the heating pad. The overall reliability of such heating pad is, therefore, probably, at best, marginal.

Heating pads have also been extensively employed in the hair curling art. See, for instance, the patent to Sartory U.S. Pat. No. 1,565,510 wherein an exothermic heater is described for generating sufficient moist heat to set a curl in hair. The device includes a porous envelope of cheesecloth or paper or the like with an inner annular layer of chemical material to react with the water to produce heat. The hair curler exothermic heaters disclosed in the art propose a wide variety of chemicals generally selected to generate sufficient heat to establish hair setting temperatures.

Another exothermic heater is disclosed in the patent to Markel et al U.S. Pat. No. 2,153,671. In this patent an aluminum foil is held between two sheets of absorbent asbestos paper and held together with suitable staples. An external impervious material such as aluminum or tin foil is coated with an inner layer of waxed or parchment paper and wrapped around the aluminum inner layer with an inner sheet of felt material to form a heating pad. A suitable chemical material is added to react with the inner located aluminum foil and generate heat.

As is typical in exothermic heaters as described in Simmons U.S. Pat. No. 1,953,513 or Mendez U.S. Pat. No. 2,612,155, the opening which permits the ingress of water or aqueous solution must be so designed to prevent the potentially toxic reacting mixture from reaching the body surface of the user. Generally, complex water enclosures are employed to prevent injury to the user.

Another difficulty recognized with exothermic heating pads involves control over the reaction. Glasser U.S. Pat. No. 3,301,250 acknowledges this and teaches the use of a plastic bag to limit the access of air to the reaction site. The opening into the plastic bag is varied to regulate the reaction speed. The plastic bag further serves to retain moisture whose evaporation would result in a termination of the heat producing reaction.

Other moist heat generators found in the art are of the electrolytic type of which the patent to Durham et al U.S. Pat. No. 2,014,246 is typical. In Durham a permanent hair wave forming apparatus is described wherein hair setting moist heat is generated by applying an external electrical power source across an electrolyte to cause it to heat and generate steam. The steam is permitted to contact and set a hair curl. The application of power to such electrolytic heater involves a hazardous device which is, furthermore, cumbersome to use.

Uniform and thorough mixing of dry chemical mixtures when water or some other aqueous reacting medium is added in an exothermic heating pad is not always obtained, thus resulting in the generation of so-called "hot spots" lacking uniform heating of the structure. Also, the chemical mixture often has a tendancey to cake, thus severely limiting the flexibility of the total heat pad structure and preventing its conformance to the surface which is to be treated.

Another moist heating pad is taught by the patent to Jensen U.S. Pat. No. 2,710,008 wherein a flexible water pervious envelope is described. The envelope contains a hot water retaining bentonite clay of the montmorillonite type. Hot water is introduced into the bentonite filler by immersing the entire structure into boiling water for an extended time period. Upon removal of the structure from the boiling water, moist heat is generated through radiative cooling. The Jensen structure essentially acts as a heat sink and has a bulky cumbersome size and is not a self-contained heat source.

The Jensen heating pad depends upon the availability of a supply of boiling water or other suitable heat source. In addition, such pad is elaborate to employ and needs a substantial amount of time before heat can be applied. The user of the Jensen pad is generally completely immobilized and must employ substantial protective guards such as multiple towel wraps to prevent burning of body surfaces as a result of the boiling point temperature of the bentonite clay.

Another type of heat source is described in the patent to Kober U.S. Pat. No. 3,774,589 assigned to the same assignee as of this application. In the Kober structure an electrochemical cell is provided with discrete electrically located shorts to generate internal heating of the cell when it is activated by the addition of water. The electrochemical cell structure is of a non-toxic design and employs a safe electrolyte to enable one to employ such structure as a heating pad for the human body.

SUMMARY OF THE INVENTION

In a self-contained therapeutic heating pad in accordance with the invention, a multi-layered heating pad structure is formed which is of flexible design to enable it to conform to a body surface. An inner layer is formed composed of a plurality of spaced heat cells. The heat cells may be of the exothermic type or of the electrochemical type disclosed in the aforementioned Kober patent. These heat cells are distributed over an inner porous layer which retains a sufficient quantity of activating liquid to fully utilize the active materials in the heat cells. The inner layers are covered by an outer sponge-like layer to form a composite pad structure capable of retaining a sufficient amount of water for transfer of heat.

A heating pad formed in accordance with the invention provides a convenient and safe source of heat with a structure that conveniently adapts to the shape of the body surface which needs to be treated. The flexibility is obtained by distributing the heat cells over the inner porous layer. The latter is sized selectively with respect to these cells to provide sufficient water storage capability to replenish the activating liquid within the cells until the active segments of the cell structure have been converted to heat. In this manner an extended time period for the generation of heat is obtained.

The foam-like outer layer provides a soft and cushion-like surface for both the retention of water and the subsequent transfer of heat from the inner located distributed heat cells to the body to be treated. The foam-like outer layer is porous to retain a desired quantity of water. When the heat cells are in the form of electrochemical cells utilizing an air depolarized cathode, the porosity of the outer foam-like layers is further selected to enable air to reach the inner structure.

The entire heating pad structure is convenient to manufacture and provides an attractive heat source for use in treating the body surface with moist heating treatments. It is, therefore, an object of the invention to provide a therapeutic moist heat pad which is safe to use in contact with a human body and convenient to apply and conform to body surfaces to be treated. It is a further object of the invention to provide a therapeutic moist heat pad of a disposable type for enhanced hygienic use while providing a uniform heating surface.

BRIEF DESCRIPTION OF DRAWINGS

These and other advantages and objects of the invention can be understood from the following detailed description of a preferred embodiment described in conjunction with the drawings wherein FIG. 1 is a perspective broken-away view of a therapeutic moist heating pad in accordance with the invention;

FIG. 2 is a top plan view of the moist heating pad shown in FIG. 1;

FIG. 3 is a section view taken along the lines 3—3 in FIG. 2 of the moist heat pad structure shown therein; and FIG. 4 is a partial section view of the moist heating pad structure shown in FIG. 2 and is a view taken along the lines 4—4 in FIG. 2.

DETAILED DESCRIPTION OF EMBODIMENT

With reference to FIG. 1, a therapeutic moist heat pad 10 is shown formed of a generally rectangular multilayered structure. Other shapes could be employed such as round or square or others as may appear desirable. The heating pad 10 is normally retained in a hermetically sealed container 11 formed by sealing a pair of impervious sheets together around a peripheral edge 13. The container 11 is provided to enable long term dry storage of the heating pad structure 10.

The heating pad structure 10 includes a pair of outer layers 12-12' formed of foam-like porous or open-celled material capable of enabling air and water to pass through towards inner layers as well as retain water.

The outer layers 12-12' enclose an inner layer of a porous felt material 14 on which a layer 16 of a plurality of electrochemical heat cells 18 are distributed. The electrochemical heat cells 18 are preferably of the type as described in greater detailed in the aforementioned Kober patent. However, it should be understood that segmented exothermic heating cells requiring a supply of activating liquid may be used in the heating pad structure.

In the embodiment shown in FIG. 1 the electrochemical heat cells 18 are shown formed of an electrochemical structure including an electrochemically active reducible element 20 and an electrochemically active oxidizable element 22. The reducible elements 20 in the illustrated embodiment are formed of an air depolarized cathode on which another material such as oxygen is reduced. The oxidizable element 22 is formed of a foil material made of aluminum or magnesium or an alloy of these latter materials.

Elements 20 and 22 are spaced from each other with a separator which in the illustrated embodiment is a sheet of bibulous material 14 such as felt, capable of absorbing and holding a substantial quantity of water. The porous layer 14 preferably is a single continuous piece upon which the electrochemical cells 18 are distributed. Preferably the electrolyte forming salt is incorporated in dry granulated form with or adjacent to the reducible element 20 to thereby avoid the need to impregnate the inner porous pad 14 while allowing the latter to serve as a protective barrier between the salt and the oxidizable element 22. With such protective barrier the oxidizable element can be preserved for an extended dry storage life of the heating pad structure 10. Alternatively the porous separator pad 14 may be selected capable of being impregnated or coated with dry electrolyte salts.

In the preferred form of the heating cells 18 the electrolyte salt is applied uniformly into the cathode or reducible element 20 structure. In the case of an air depolarized cathode using activated carbon, the table salt is orginally uniformly dry mixed with the activated carbon in the range of about one to two and a half grams of sodium chloride to about 1 gram of carbon. Although higher and lower ratios of table salt to carbon can be used, a ratio of about 1.5-1.7 grams of table salt to 1 gram of carbon is preferred.

In the case of a reducible element 20 formed of manganese dioxide, an electrolyte salt such as dry granular table salt is premixed in the ratio of from about 1 to 2½ grams of table salt to about 1 gram of manganese dioxide. Although higher and lower ratios of table salt to manganese dioxide can be used, a ratio of about 1.5 grams table salt to 1 gram of manganese dioxide is preferred.

The incorporation of the dry electrolytic salt into the reducible element 20 structure provides a particularly enhanced performance of the air depolarized activated carbon cathode structure. The electrolyte salt is leached out of the carbon structure during activation to thus provide a larger surface area on which oxygen can be reduced.

Suitable shorting elements 24 in the form of staples electrically short elements 20, 22 to each other to enable a heating current flow when the electrochemical heat cells 18 are activated while also serving to hold the heat cells 18 together.

The selection of materials and configurations for the elements 20, 22 and separator 14 may vary depending upon the desired type of electrochemical heating cells. Various types are enumerated in the aforementioned Kober patent to which reference can be made for further details. A preferred composition of the electrochemical heat source for use in the moist heat pad 10 would be a metallic magnesium anode foil 22 and a cathode 20 of the carbon-air depolarized type or a manganese dioxide depolarizer with both using a sodium chloride (table salt) electrolyte salt.

The outer porous layers 12-12' are joined to each other with a suitable adhesive such as a line of glue 26 (see FIGS. 2, 3 and 4) applied around the periphery between the outer layers 12-12' so that the entire moist heating pad appears as an integral structure with the heat cells 18 fully enclosed.

As shown in FIGS. 3 and 4, a pair of thin films 28-28' of impervious material such as polyethelene are laminated to the outer porous layers 12-12'. The polyethelene films 28 have a thickness of the order of a fraction of an inch, preferably about one thousandth of an inch thick, to control the electrochemical reaction by reducing the amount of air reaching the electrochemical cells 18. Films 28-28' thus help to extend the heat generating period while being sufficiently thin to permit heat to transfer through the films 28 onto the body surface to be treated. The polyethelene films 28 provide a hygienic and smooth touch to the entire heating pad structure. Since films 28 are effective sealers, they are punctured at a plurality of distributed places as shown with apertures 30 to assure that a moisture coating is formed between the film 28 and the body surface to be treated. Apertures 30 extend partially into the outer porous layers 12-12'.

With the therapeutic heating pad structure 10 extended heating periods can be obtained depending upon the overall size of the heating cells 18 and the amount of activating liquid or electrolyte available to convert the electrochemical or exothermic energy in the cells to heat.

The selection of the inner porous pad 14 includes such considerations as the amount of activating liquid such as water that must be absorbed to assure an adequate supply throughout the activation of the heating cells. For example, an absorption capability of at least 20 grams of water per cubic inch is generally sufficient for most applications involving an electrochemical heating cell 18. The materials of which the porous pad may be made can be such as felt, cotton or bibulous papers. However, from the point of view of water absorption rate, water holding capability and ease of handling and manufacture, cotton based porous bibulous pads and felts are preferred. Bibulous papers can conveniently provide control over the heat rate generation by selection of the number of paper layers to be used with any one particular heating pad structure.

The porous pad 14 is further selected in size to assure an adequate storage of electrolyte to supply to the electrochemical cells 18. The relative area of the porous pad to the total area of the electrochemical heat cells 18 is generally selected in the ratio from about 1.5 to 1 to about 4 to 1 with a generally uniform crossection of a sheet of porous pad. Generally, within the limits of such range, an adequate amount of electrolyte can be retained and supplied by a capilliary wicking action to the several electrochemical heat cells without an excessive, hard to accommodate, physical size.

The larger area of the porous pad 14 relative to the total area of the electrochemical cells advantageously enables a segmentation and separation of the electrochemical heat cells 18. In this manner an extended supply of electrolyte is available to the cells 18 while at the same time providing a flexible therapeutic pad structure which can conform to the body surface to be treated. When the porous pad is properly sized, optimum therapeutic heating pad surface temperatures of about 100° to about 185° F can be maintained for treatment of a body surface. The surface temperature of the pad depends upon the desired therapeutic application and can be arranged accordingly by selecting the size and number of heating elements. The heating pad structure according to this invention has been found capable of providing an adequate amount of moist heat to maintain a therapeutic skin temperature.

In some instances it may be desirable to provide a therapeutic heating pad whose temperature rise is moderated and whose final heating temperature is lowered. One approach to achieve this is by making a porous pad 14 larger and correspondingly provide larger outer layers 12-12'. This would result in a greater amount of water in the entire heating pad structure 10. All of this water would then have to be heated by the heat cells 18 which achieve the more moderate therapeutic temperatures over a longer time.

In one example for a therapeutic moist heating pad in accordance with the invention and as shown in the figures, six electrochemical heat cells of the air-depolarized cathode and magnesium foil type were used with area dimensions for each of about 1 by 1 inch. The porous pad layer 14 was made of felt about one-sixteenth of an inch thickness and generally rectangularly shaped with dimensions of 3 inches by 5 inches. The electrochemical cells 18 were spaced from each other as shown, each surrounded by the porous pad from which additional electrolyte may be wicked for use in cells 18.

The porous separator pad 14 preferably is a continuous sheet with the electrochemical heat cells being attached as shown. In this manner electrolyte for the individual heat cells 18 may be drawn from surrounding areas. The porous pad 14, however, may be split lengthwise with three electrochemical cells 18 mounted in a row.

The amount of salt used in each of the electrochemical cells 18 was about 0.45 grams. The quantity may vary, depending upon the area ratio between the porous pad 14 and the total area of the electrochemical heat cells 18.

In an alternate approach, activation of the therapeutic heating pad 10 may be obtained by dipping the structure 10 in a solution of water and table salt wherein the salt concentration is selected to establish generally the same electrolyte as when the table salt is incorporated with the reducible element or cathode structure 20.

The selection of outer porous layers 12-12' involves considerations such as their ability to enable atmospheric oxygen to reach the enclosed electrochemical heat cells 18 and the rate at which heat is transferred to the outside of the structure. The number of pores per inch (ppi) and size of the pores in the layers 12 thus is a factor as well as the requirement for an open-celled material. In some applications a single outer layer 12' of sponge-like porous material may be used such as on the side of the electrochemical heat cell where an air depolarized cathode is used. In such case the other outer layer 12 may be replaced with a suitable cover of a harder material as may appear appropriate.

One material which has been found particularly useful for a layer 12 is a flexible polyurethane foam. Such foams are commercially available in a wide range of thicknesses, finishes, colors and pores per inch. The size and thickness and overall volume of the layers 12-12' establish a maximum water retention capability. Generally, the actual water retained is somewhat less than the maximum since the user generally prefers a less saturated therapeutic pad to prevent an unplesant run-off of water over the body. The reduction of the amount of water can thus be taken into account in the sizing of layers 12-12' keeping in mind that the larger amount of normally retained water results in a greater load on the heat cells 18 with an attendant reduction of a high temperature sustaining capability. An increase in high temperature heating can be obtained by employing preheated water to activate the structure. However, the availability of a hot water supply cannot always be relied upon.

In the aforementioned example for a therapeutic moist heating pad, a pair of outer layers 12-12' of polyurethane foam were employed with a porosity of about 100 pores per inch. The thickness of the layers was each about one quarter of an inch and each layer was 4 by 6 inches in area. The layers 12-12' were each covered with a laminate layer 28 of polyethylene of one thousandths of an inch thick which was punctured with eleven apertures 30 of about one eighth of an inch diameter and extending partly into layers 12. The layers 12 were sufficiently large to be joined to each other with a solvent base or hot melt adhesive as is well known for use in attaching polyurethane foams. The layers 12 may be stitched to each other or as may appear desirable in certain cases, heat sealed together.

The self contained therapeutic moist heat pad 10 as described is conveniently activated by immersion in water. The highly flexible structure conveniently enables the introduction of water by gentle squeeze action to create a pumping action. Within a short time of about 30 seconds, the inner porous pad 14 has absorbed a sufficient quantity of water to initiate and sustain the heat generating action of the electrochemical heat cells 18.

The degree of wetness of the moist heat pad can be a matter of personal preference to the user by controlling the water retained by the open cell outer layers 12-12'. Gentle pressing of the structure removes excess water without causing a removal of water from the inner porous pad 14. Hence, the heat generation from the electrochemical heat cells is generally unaffected by the user's personal preference for the wetness of the pad. At the same time, any reaction products formed at the heat cells are retained by porous pad 14 by virtue of its high absorption characteristic. Hence, any allergic reaction causing products are absorbed at the reaction site and precluded from transport to the body surface being treated.

Having thus described a therapeutic moist heat pad structure in accordance with the invention, its many advantages can be appreciated. An attractive hygienic moist heat source is provided which may conform to the body surfaces. Extended heat treating periods can be obtained with temperatures of 160° F being maintainable for periods of the order from about 30 minutes to well over 1 hour.

What is claimed is:

1. In a self contained therapeutic moist heating pad the improvement of a multilayered heating pad structure comprising an inner located segmented heating source formed of a plurality of distributed liquid accessible heat producing cells spaced from each other to achieve uniform heating of the pad surface with enhanced heating pad flexibility for conformance to a body surface to be treated;

an inner located porous layer formed of a liquid absorbent material located for surface wicking contact with the liquid accessible distributed heat cells to supply activating liquid thereto;

a flexible moisture and air permeable non-metallic sponge-like external layer located and coupled to enable liquid to reach the heating cells through the external layer for activation of the cells and for storage of liquid in the inner porous layer while providing a moist heat transfer path from the heating cells to an external surface of the external layer to form said moist heating pad structure.

2. The improved self contained therapeutic moist heating pad as claimed in claim 1 wherein the inner located porous layer extends in area around the heat producing cells to provide a reservoir of activating liquid to the heating cells.

3. The improved self contained moist heating pad as claimed in claim 2 wherein the inner located porous layer is attached to the heat producing cells for spatially distributive support thereof.

4. The improved self contained moist heating pad as claimed in claim 3 wherein the heating pad structure further is provided with a thin apertured moisture barrier overlying the permeable external flexible layer provided with a sufficient number of apertures to enable moisture to pass therethrough for moisture wetting of the external barrier surface, said barrier further being made sufficiently thin to enable a transfer of heat to the moisture on the external barrier surface.

5. A multilayered heating pad structure including an inner located layer of a segmented heat source formed of a plurality of distributed heat producing liquid accessible cells for uniform heating of the multilayered pad structure, said heat producing cells being selected to be activated for the generation of heat upon the addition of an activation liquid;

an inner located flexible layer of porous liquid absorbent material selectively sized to retain said activating liquid needed to achieve prolonged generation of heat from the cells at therapeutic temperatures, said inner located flexible liquid absorbent layer being in wicking contact with the cells to provide a supply of liquid thereto for extended heat generation; and an outer layer of sponge-like flexible material sized and shaped to overlie the inner layers and being formed of a porous material selected to enable liquid and air to reach the inner layers through the outer layer for activation of the distributed cells and while providing a moist heat transfer path from the heat producing cells to an external body contacting surface to form said moist heating pad.

6. The self contained therapeutic moist heating pad as claimed in claim 5 wherein the outer layer of sponge-like flexible material extends to overly opposite sides of the inner layers to form a sandwich shaped moist heating pad structure.

7. The self contained therapeutic moist heating pad structure as claimed in claim 5 wherein the heat cells are each formed of electrochemical heat cells mounted in a distributive manner on the inner porous layer.

8. The self contained therapeutic moist heating pad as claimed in claim 7 wherein the electrochemical cells are each formed of electrochemically active oxidizing element and an electrochemically active reducing element, and wherein said inner layer of porous material is located and extends between the elements of the electrochemical cells to provide an extended separator for electrochemical energization of the cells upon the addition of water.

9. The self contained therapeutic moist heating pad as claimed in claim 8 wherein the multilayered heating pad structure includes a pair of outer layers of sponge-like material which are attached to each other around the peripheral edge of the multilayered pad structure to enclose the inner layers.

10. The self contained therapeutic moist heating pad as claimed in claim 7 wherein the electrochemical cells are each formed with an air-depolarized cathode, and wherein the outer layer of sponge-like material overlies the air-depolarized cathodes of the cells.

11. The self contained therapeutic moist heating pad as claimed in claim 10 wherein said one outer layer of sponge-like material which overlies the air-depolarized cathode has an effective porosity of air selected to regulate the access of air to the cathode for control of the rate of heat generated by the multi-layered heating pad structure.

12. The self contained therapeutic moist heating pad as claimed in claim 11 wherein said one outer layer of sponge-like material is further characterized with a porous structure having a predetermined thickness and a predetermined number of pores per inch selected to provide the desired heat generation and water retention.

13. The self contained therapeutic moist heating pad as claimed in claim 12 wherein said outer layer of sponge-like material is further provided with thin, generally non-porous apertured overlying films of material selected to reduce the access of air to the cathode and provide a smooth tactile characteristic to the multilayered heating pad structure.

14. The self contained therapeutic moist heating pad as claimed in claim 7 wherein the surface area ratios between the electrochemical cells and the inner porous layer is in the range of about 1 to 1.5 to about 1 to 4 for enhanced utilization of electrochemical materials while producing a sufficient amount of heat to increase the temperature of the heating pad structure to a therapeutically usable level for a satisfactory duration.

15. The self contained therapeutic moist heating pad as claimed in claim 14 wherein the unfilled spatial volume ratio between the outer layers of sponge-like material and the inner layer of porous material is in the range of about 12 to 1 to about 12 to 4 to provide said therapeutically usable temperature level.

16. In a self contained heating pad formed with an electrochemical heat cell using an anode member, a cathode member and short elements connected thereto, the improvement comprising a cathode member formed with an electrochemically active reducible material intermixed with a dry electrolyte material.

17. The improvement as claimed in claim 16 wherein the cathode member is of the air depolarized type.

18. The improvement as claimed in claim 17 wherein the electrochemically active reducible material is activated carbon and wherein the dry electrolyte is intermixed with the activated carbon.

19. The improvement as claimed in claim 18 wherein the dry electrolyte is formed of sodium chloride.

20. The improvement as claimed in claim 16 wherein the electrochemically active material is manganese dioxide.

21. A dry stored self contained heat generating pad comprising
a multilayered heating pad structure including an electrochemical heat cell formed of an air depolarized activated carbon electrode, an anode member and a separator therebetween, and a dry electrolyte intermixed with the activated carbon for enhanced cathode performance upon activation of the heat cell by submersion of the heat cell in a liquid to dissolve the dry electrolyte.

22. In a self contained heating device formed with an electrochemical heat cell using an anode member, a cathode member and shorting elements connected thereto, the improvement comprising a cathode member formed with an electrochemically active reducible material intermixed with a dry electrolyte material.

23. The improvement as claimed in claim 22 wherein the dry table salt is provided in an amount of about from 1 to 2½ grams table salt to about 1 gram of electrochemically active reducible material.

24. The improvement as claimed in claim 23 wherein the dry table salt is provided in an amount of about 1.5 grams of table salt to each gram of electrochemically active reducible material.

25. The improvement as claimed in claim 22 wherein the cathode member is an air depolarized activated carbon cathode, with dry table salt intermixed with the activated carbon.

26. The improvement as claimed in claim 22 wherein the cathode member is formed with an electrochemically active reducible material of manganese dioxide intermixed with dry table salt.

* * * * *

Disclaimer and Dedication

4,106,477.—*Sheldon L. Feld*, Jamaica, N.Y. THERAPEUTIC SELF-GENERATING MOIST HEAT PAD. Patent dated Aug. 15, 1978. Disclaimer and Dedication filed June 23, 1983, by the assignee, *Chem-E-Watt Corp.*

Hereby disclaims and dedicates to the Public the entire remaining term of said patent.

[*Official Gazette August 16, 1983.*]